United States Patent [19]

Ignasiak

[11] 4,324,331
[45] Apr. 13, 1982

[54] PACKAGING FOR SURGICAL IMPLEMENTS

[75] Inventor: Michael J. Ignasiak, Warsaw, Ind.

[73] Assignee: Zimmer, Inc., Warsaw, Ind.

[21] Appl. No.: 176,368

[22] Filed: Aug. 8, 1980

[51] Int. Cl.³ .................... B65D 85/20; B65D 85/24; B65D 81/04

[52] U.S. Cl. .................... 206/363; 206/368; 206/461; 206/591; 206/370

[58] Field of Search ............ 206/365, 370, 328, 332, 206/464, 461, 806, 814, 207, 349, 363, 368, 591

[56] References Cited

U.S. PATENT DOCUMENTS

| | | | |
|---|---|---|---|
| D. 253,751 | 12/1979 | Meierhoefer | D9/192 |
| 2,280,573 | 4/1942 | Flaws, Jr. | 206/328 |
| 2,346,636 | 4/1944 | Porter | 206/12 |
| 2,903,139 | 9/1959 | Penman | 206/332 |
| 3,013,656 | 12/1961 | Murphy, Jr. | 206/72 |
| 3,047,139 | 7/1962 | Jacoff | 206/806 |
| 3,318,499 | 5/1967 | Kallio | 206/349 |
| 3,329,261 | 7/1967 | Serany, Jr. et al. | 206/229 |
| 3,346,100 | 10/1967 | Carlson | 206/207 |
| 3,369,043 | 3/1975 | Warner et al. | 206/464 |
| 3,410,395 | 11/1968 | Sellers | 206/439 |
| 3,485,352 | 12/1969 | Pilger | 206/365 |
| 3,697,223 | 10/1972 | Kovalcik et al. | 21/83 |
| 3,770,119 | 11/1973 | Hultberg et al. | 206/63.2 R |
| 4,216,860 | 8/1980 | Heimann | 206/370 |

*Primary Examiner*—William T. Dixson, Jr.
*Attorney, Agent, or Firm*—Margaret L. Geringer

[57] ABSTRACT

The present invention relates to a storage container for pre-sterilized surgical implements. The container is comprised of a bottom assembly containing at least one cavity for receiving a surgical implement such as a drill bit, pin or wire and a lid portion which is heat sealed onto the bottom assembly such that it acts as a sterile barrier in containing the product.

The invention utilizes a plurality of areas spaced apart longitudinally in the cavity for selectively placing protective plugs at each end of the implement such that one packaging cavity may be used for various lengths of implements. The protective plugs prevent the implement from penetrating the ends of the cavity which would break the sterile barrier.

9 Claims, 6 Drawing Figures

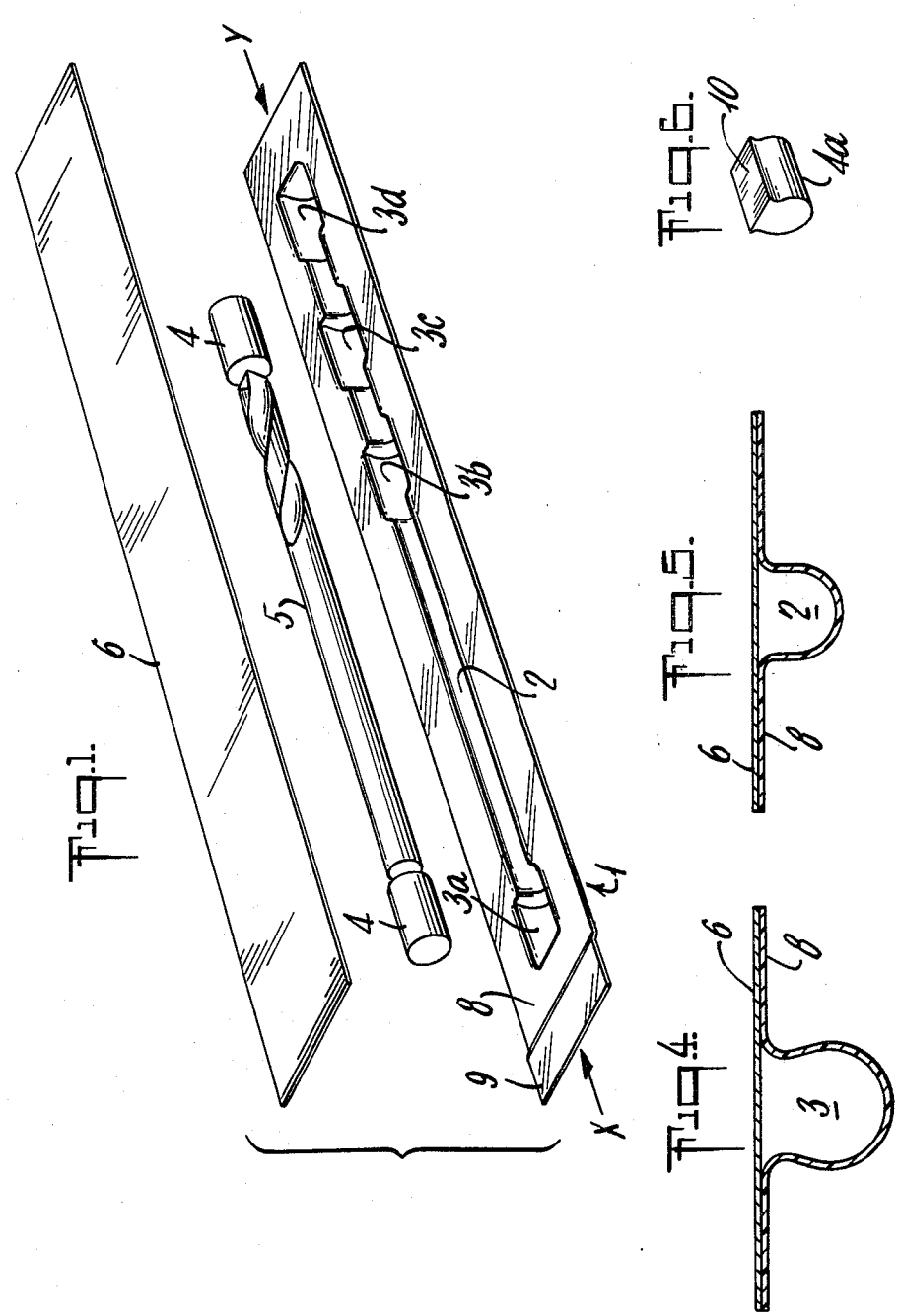

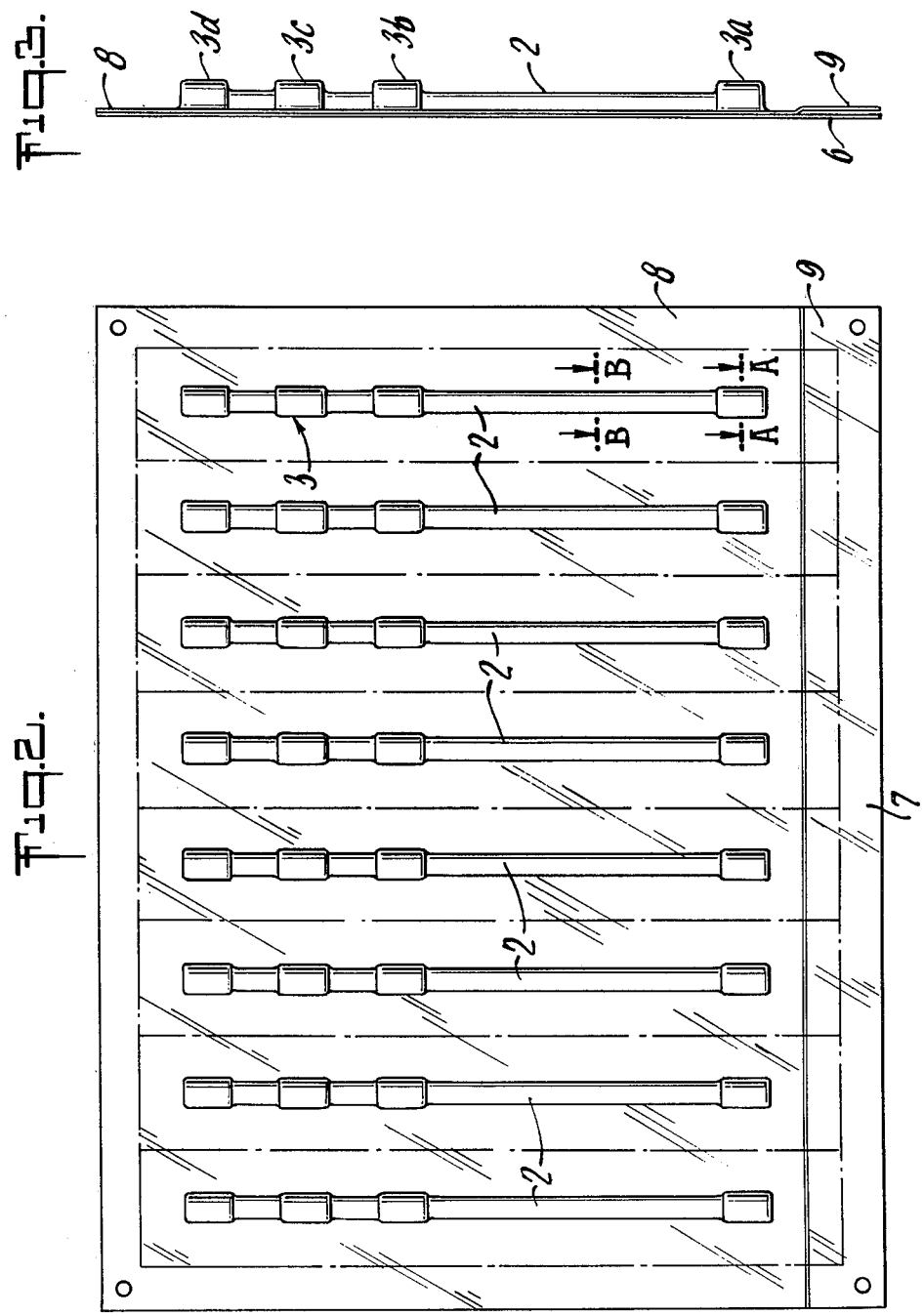

PACKAGING FOR SURGICAL IMPLEMENTS

BACKGROUND OF THE INVENTION

The packaging concept of a plastic blister or cavity for a bottom assembly with a lid portion which is heat sealed to act as a sterile barrier to contain a product is known in the art. The lidding stock typically used for this type of packaging is TYVEK ® spun bound polyolefin. TYVEK is a registered trademark of Dupont. This type of pre-sterilized packaging does not provide a means of preventing the product from contacting the wall of the cavity. The product is usually placed in this type container with no additional packaging materials. A sharp product such as a drill bit or heavy pin could normally vibrate against the cavity wall and either penetrate the cavity, which would break the sterile barrier, or contact the cavity enough to generate plastic flasks of the cavity material on to the product.

The use of protective materials to prevent sharp product tips from contacting a package is also known in the art. An example of this is products which are packaged in open-ended cylindrical tubes such that a cylindrical section of foam is placed at each end of the tube after the product is placed within the tube, and then each end is capped. This particular type of packaging is not suitable for pre-sterilization.

OBJECTS OF THE INVENTION

The principle object of the invention is to provide a container which is suitable for protectively packaging various lengths of product in the same style container. This prevents having separate cavities or blisters manufactured for each individual length of product.

A further object of this invention is to provide a simple packaging container suitable for pre-sterilization which contains a protective means within the cavity for preventing the ends of sharp instruments from contacting the wall of the cavity. This prevents the sharp distal tip and the proximal end from penetrating the cavity, and thus breaking the sterile barrier, and also prevents the ends from contacting the cavity enough to generate flasks of the cavity material onto the product.

A still further object of the invention is to provide a simple protective means within the cavity such that when the lidding stock is peeled off to dispense the sterile product, the protective means remain within the cavity so that it does not fall onto the sterile field.

BRIEF SUMMARY OF THE INVENTION

The present invention accomplishes all of the above objects of the invention. The pre-sterilized storage container for surgical instruments utilizes protective plugs which can preferably be snapped into the appropriate areas provided in the cavity of a thin plastic bottom assembly which is heat sealed with a heat sealable lidding stock.

The bottom assembly is manufactured so that the cavity includes a number of areas capable of containing a protective plug. This allows the same style of bottom assembly to be used for various lengths of products. The plugs are placed so that the cavity space for the product is only slightly longer than the product itself. This prevents having too much room for the product to slide back and forth. The lid portion is then heat sealed onto the bottom assembly.

Protective plugs are placed in the appropriate areas at each end of the product to prevent the ends of the product from contacting the end wall of the cavity. The protective plug allows the point of a product to contact it, and therefore it should be soft enough not to damage the product tip, yet rigid enough not to generate particulate flakes onto the product itself. Protective plugs which snap into the areas provided for them are particularly advantageous because they will remain in that area when the package is opened, and therefore not fall onto a sterile field with the sterile product.

BRIEF DESCRIPTION OF THE DRAWINGS

In order that the principles of the present invention may be readily understood, one particularly advantageous embodiment of the invention will be described with reference to the accompanying drawings, which form part of the original disclosure of this application, and wherein:

FIG. 1 is an exploded pictorial assembly view illustrating the bottom assembly, a sample product, two protective plugs and the lidding stock.

FIG. 2 is a top view illustrating a bottom assembly containing eight cavities for implements.

FIG. 3 is a side view of the bottom assembly of FIG. 2.

FIG. 4 is a cross-sectional view taken at section-AA of FIG. 2 illustrating the cross-section of an area for the snap-in protective plugs.

FIG. 5 is a cross-sectional view taken at section-BB of FIG. 2 illustrating the cross-section of the main cavity.

FIG. 6 is a perspective view of an alternate embodiment of the protective plug.

DETAILED DESCRIPTION OF THE INVENTION

FIG. 1 illustrates a particularly advantageous embodiment of the present invention of a storage container for pre-sterilized surgical implements. The container is comprised of a bottom assembly 1 and two protective snap-in plugs 4 and a lid portion 6 which is to be heat sealed to the bottom assembly 1 to contain a product 5.

The bottom assembly 1 can be formed from any thermoformable plastic material adaptable to sterile packaging. An example of this type of plastic is XT ® polymer film. XT is a registered trademark of CYRO Industries, a partnership of Cyanamid Plastics, Inc. and Rohacryl, Inc. Another example of a suitable material for the bottom assembly is KODAR ® PETG Copolyester 6763. KODAR is a registered trademark of Eastman Kodak Company. The bottom assembly 1 is basically a thin, flat, usually rectangular, sheet of this plastic material into which an integral cavity 2 is depressed into the flat portion 8. The cavities 2 or blisters are usually manufactured by thermoforming the plastic film to various configurations, and therefore are capable of containing any shape product. The preferred embodiment of this invention utilizes this cavity 2 for such long thin surgical implements as drill bits, pins or wires.

Therefore, to accommodate such implements, the depressed cavity 2 is long and thin and preferably substantially cylindrical in shape with one longitudinal side of the cylindrical shape open to receive an implement. The cross-section of the cavity 2 is illustrated in FIG. 5.

The cavity 2 of the preferred embodiment, as shown in FIG. 1, contains four areas 3 capable of containing snap-in protective plugs 4. The areas 3 in this embodiment, are substantially cylindrical in shape with one longitudinal side of the cylindrical shape open for receiving a plug. At least more than half of a cylindrical shape is present in the area 3 to allow for a cylindrical plug 4 to be locked securely into place in the area 3. A cross-section of the plug area 3 is illustrated in FIG. 4. The plug areas 3 and the plugs 4, which mate snugly into said plug areas 3, are larger in diameter than the overall cavity 2 to lodge the plugs 4 laterally in place.

In the preferred embodiment, the snap-in protective plugs 4 are substantially cylindrical shape. Said plugs 4 snap-lock into the appropriate areas 3 in the bottom assembly. Any shape plug 4 and corresponding area 3 for said plug which is adaptable to a snap-lock fit is suitable. FIG. 6 illustrates an alternate shape for the snap-in protective plug 4a. Although it is still substantially cylindrical in shape, the plug includes a flat plane 10 along a longitudinal side of the plug 4a. This allows the flat plane 10 of plug 4a to be flush with the flat area 8 of the bottom assembly 1.

The plugs 4 are preferably made of any material, such as plastic or rubber, which is soft enough not to damage the trip of the product 5, yet rigid enough not to generate particulate flakes onto the product itself. The snap-fit of the plug 4 prevents it from falling onto a sterile field with the product 5 at the time of dispensing. A protective plug 4 snapped into place at each end of the product 5 prevents the sharp tip of the product from contacting the end walls of the cavity 2. A sharp product such as a drill bit or heavy pin could normally vibrate against the cavity wall and either penetrate the cavity 2, which would break the sterile barrier, or it would contact the cavity enough to generate plastic flakes of the cavity material onto the product 5. Use of the protective plugs 4 prevents this.

FIG. 1 illustrates the multiple areas 3b, 3c and 3d at the first end Y of the cavity 2 spaced apart longitudinally from each other, and one area 3a at the second end X of the cavity 2. The use of the multiple areas 3 at least one end of the cavity allows the same style of bottom assembly 1 to be used for various lengths of implements.

For example, the same bottom assembly 1 could be used for a three inch, four inch or five inch long implement. In each case, a protective plug 4 is snapped into area 3a. For the three inch implement, the second plug 4 would be snapped into area 3b. For a four inch implement, the second plug would be snapped into area 3c. For a five inch implement, the second plug would be snapped into area 3d. This illustrates how the same bottom assembly 1 can be used for more than one length of implement.

The areas 3 for the plugs 4 are spaced so that the cavity 2 for a product 5 is only slightly longer than the product itself to prevent the product 5 from being able to slide back and forth any more than minimal.

After the product 5 is placed in the cavity, with a plug 4 snapped into an area 3 at each end of the product, the lid portion 6 is placed over the bottom assembly 1 so as to cover the opening of the cavity 2. The lid portion 6 can be made of any heat sealable material. A spun bound polyolefin material, such as TYVEK ® spun bound polyolefin is particularly suitable for the lidding material. Other materials such as laminated surgical grade paper or plastic film could also be used. The lid portion 6 is a thin, flat, usually rectangular, sheet of this heat sealable material which has the same outer shape as the flat portion 8 of the bottom assembly 1. The lid 6 is heat sealed onto the bottom assembly 1.

At one end of the bottom assembly 1, the flat area 8 is depressed to a slightly lower level 9. This lower portion 9 does not get sealed to the lid 6, and therefore, the unsealed end of the lid 6 can be used as a tab for conveniently tearing off the lid 6 from the bottom assembly 1 when the package is ready to be opened.

After the lid portion 6 is heat sealed to the bottom assembly 1, the complete sealed package containing the enclosed product is then ready for sterilization. It has been found that gamma radiation is a good sterilization method for this type of packaging. The gamma radiation sterilizes the product and product environment. The heat-sealed lid 6 acts as a sterile barrier in containing the product. Other forms of sterilization, such as ethylene oxide sterilization, could also be used.

The product is now pre-sterilized and ready for surgical use. When the product is ready for use, the lid 6 is peeled away from the bottom assembly 1 to dispense the product. The protective plugs 4 remain snapped in place so that they do not fall onto the sterile field with the product. This packaging concept is easily adaptable to disposable products.

The package assemblies may be manufactured as individual units or in multiple units. FIG. 2 illustrates a sheet of eight bottom assemblies. If packages are manufactured as multiple units, individual units can be punched out on a steel rule die by a clicking press or perforations can be made between individual assemblies to allow single packages to be dispensed. Other methods would also be suitable.

A further embodiment of the invention could be to remove the area 3a at the second end X of the cavity 2. This embodiment could be used with a product that has a sharp end and a blunt end. The blunt end could go at the second end X of the cavity 2 with the sharp end at the first end Y of the cavity 2. The sharp end would be protected by a protective plug 4. This embodiment still utilizes the inventive feature of the multiple areas 3 spaced at one end of the cavity to accommodate various sizes of product and protect the sharp end of the product. This embodiment which protects only the sharp end of a product is not as protective because the blunt end could still potentially break through the cavity due to vibration or shock if not protected by a plug 4.

The invention described here relates to a storage container for pre-sterilized surgical implements. The container utilizes protective plugs for preventing the implement from vibrating against the wall of the storage cavity. The container is especially adaptable for any product with a sharp point or edge, especially long thin products such as drill bits, pins or wires. The container is adaptable for use with more than one size of product and is also easily adaptable for use with disposable products.

While certain preferred embodiments of this invention have been illustrated and described in the foregoing specification, it will be understood that modifications can be made without departing from the spirit and scope of the invention.

What is claimed is:

1. A storage container for rigid elongated surgical implements which is suitable for pre-sterilized packaging comprising:
   (a) a bottom assembly containing an elongated cavity for receiving an implement wherein said cavity has a first end and a second end;
   (b) a plurality of areas at the first end of said cavity spaced apart longitudinally from each other and capable of containing a protective plug, such that the plug will be retained in the area in the bottom assembly upon dispensing of the product from the container;

(c) at least one protective plug for selectively positioning in at least one of said areas in order to selectively accommodate various length implements in the cavity, while restricting the amount of longitudinal movement of the implement in the cavity and protecting the implement from hitting the end of the cavity, each said plug being made of any suitable material soft enough not to damage the surgical implement, yet rigid enough not to generate particulate flakes onto the surgical implement; and (d) a lid portion capable of being sealed to the bottom assembly to retain the implement until ready for dispensing.

2. A container as defined in claim 1 wherein the second end of said cavity of the bottom assembly further includes at least one area capable of containing a protective plug, and includes at least one additional plug for positioning in said at least one area at the second end of the cavity.

3. A container as defined in claim 1 wherein the bottom assembly is a thin flat sheet of material with one or more integral cavities depressed into the material and wherein said cavities are conformed to the general shape of the product contained.

4. A container as defined in claim 1 wherein said cavity is long and thin and substantially cylindrical in shape with one longitudinal side of the cylindrical shape open to receive an implement.

5. A container as defined in claim 1 or 2 wherein said protective plugs and the areas for containing said plugs are of a corresponding mating shape suitable for a snap lock fit to maintain the plugs securely in the areas.

6. A container as defined in claim 5 wherein said snap-in plugs are substantially cylindrical in shape and wherein said areas for snap-in plugs are substantially cylindrical in shape with one side of the cylindrical shape of the area open for receiving the plug and at least more than half of a cylindrical shape present in the area to allow for the substantially cylindrical plug to be snapped into the area.

7. A container as defined in claim 1 wherein said areas for protective plugs are larger in diameter than the overall cavity.

8. A container as defined in claim 1 wherein the bottom assembly is fabricated from any thermoformable plastic material adaptable to sterile packaging.

9. A container as defined in claim 1 wherein the lid portion is made of any heat sealable material in the shape of a thin, flat, sheet which is heat sealed to the bottom assembly and which can act as a sterile barrier in containing a product in a sterile environment.

* * * * *